(12) United States Patent
Strnad

(10) Patent No.: US 6,352,537 B1
(45) Date of Patent: Mar. 5, 2002

(54) METHOD AND APPARATUS FOR SPINAL FIXATION

(75) Inventor: Lee A. Strnad, Andover, NJ (US)

(73) Assignee: Electro-Biology, Inc., Parsippany, NJ (US)

( * ) Notice: Subject to any disclaimer, the term of this patent is extended or adjusted under 35 U.S.C. 154(b) by 0 days.

(21) Appl. No.: 09/156,543

(22) Filed: Sep. 17, 1998

(51) Int. Cl.$^7$ ............................................... A61B 17/70
(52) U.S. Cl. .......................................... 606/61; 606/72
(58) Field of Search .............................. 606/60–61, 63, 606/64, 72–73, 59

(56) References Cited

U.S. PATENT DOCUMENTS

| 4,274,401 A | 6/1981 | Miskew | 128/69 |
| 5,000,165 A | 3/1991 | Watanabe | 128/69 |
| 5,002,542 A | 3/1991 | Frigg | 606/61 |
| 5,005,562 A | * 4/1991 | Cotrel | 606/61 |
| 5,084,048 A | 1/1992 | Jacob et al. | 606/61 |
| 5,092,893 A | 3/1992 | Smith | 623/17 |
| 5,102,412 A | 4/1992 | Rogozinski | 606/61 |
| 5,122,131 A | 6/1992 | Tsou | 606/61 |
| 5,127,912 A | 7/1992 | Ray et al. | 606/61 |
| 5,129,899 A | 7/1992 | Small et al. | 606/61 |
| 5,181,917 A | 1/1993 | Rogozinski | 606/61 |
| 5,261,910 A | 11/1993 | Warden et al. | 606/61 |
| 5,344,422 A | 9/1994 | Frigg | 606/61 |
| 5,374,267 A | 12/1994 | Siegal | 606/61 |
| 5,387,213 A | 2/1995 | Breard et al. | 606/61 |
| 5,395,370 A | * 3/1995 | Muller et al. | 606/61 |
| 5,413,576 A | 5/1995 | Rivard | 606/61 |
| 5,415,659 A | * 5/1995 | Lee et al. | 606/61 |
| 5,437,671 A | 8/1995 | Lozier et al. | 606/61 |
| 5,466,237 A | 11/1995 | Byrd, III et al. | 606/61 |
| 5,474,555 A | 12/1995 | Puno et al. | 606/73 |
| 5,476,462 A | 12/1995 | Allard et al. | 606/60 |
| 5,487,742 A | 1/1996 | Cotrel | 606/61 |
| 5,501,684 A | * 3/1996 | Schlapher et al. | 606/61 |
| 5,522,816 A | 6/1996 | Dinello et al. | 606/61 |
| 5,540,688 A | 7/1996 | Navas | 606/61 |
| 5,540,690 A | 7/1996 | Miller et al. | 606/61 |
| 5,562,662 A | 10/1996 | Brumfield et al. | 606/61 |
| 5,569,246 A | 10/1996 | Ojima et al. | 606/61 |
| 5,569,247 A | 10/1996 | Morrison | 606/61 |
| 5,575,791 A | * 11/1996 | Lin | 606/61 |
| 5,575,792 A | 11/1996 | Errico et al. | 606/61 |
| 5,578,033 A | 11/1996 | Errico et al. | 606/61 |
| 5,584,887 A | 12/1996 | Kambin | 623/17 |
| 5,591,166 A | * 1/1997 | Bernhardt et al. | 606/61 |
| 5,601,552 A | 2/1997 | Cotrel | 606/61 |

(List continued on next page.)

OTHER PUBLICATIONS

Sofamor Danek brochure entitled TRSH® Spinal System, 1 page, undated.
Sofamor Danek brochure entitled CD™ Spinal System, 2 pages, undated.

Primary Examiner—Cary E. O'Connor
(74) Attorney, Agent, or Firm—Harnes,, Dickey & Pierce, P.L.C.

(57) ABSTRACT

An apparatus for a spinal fixation generally includes a hook member and a linkage. The hook member includes an upper portion and a lower portion. The lower portion has a generally arcuate shape and defines an aperture passing therethrough. The lower portion has a curved shape for engaging the lamina. The linkage includes a generally flat plate and defines an arcuate service for matingly receiving the upper portion of the hook member so as to permit relative rotation therebetween. The apparatus further includes a coupling arrangement including a shaft passing through the recess of the linkage and an aperture of the hook member. The shaft includes an upper end and a lower end. A locking member is carried by a lower end and disposed within an aperture of the hook member. A nut is provided in threaded engagement with the upper end of the shaft.

20 Claims, 4 Drawing Sheets

U.S. PATENT DOCUMENTS

| | | |
|---|---|---|
| 5,609,592 A | 3/1997 | Brumfield et al. ............ 606/61 |
| 5,628,740 A | 5/1997 | Mullane ...................... 606/61 |
| 5,630,816 A | 5/1997 | Kambin ....................... 606/61 |
| 5,634,925 A | 6/1997 | Urbanski ..................... 606/61 |
| 5,688,272 A * | 11/1997 | Montague et al. ............ 606/61 |
| 5,725,528 A | 3/1998 | Errico et al. .................. 606/61 |
| 5,752,957 A * | 5/1998 | Ralph et al. .................. 606/61 |
| 5,810,818 A * | 9/1998 | Errico et al. .................. 606/61 |
| 6,123,706 A * | 9/2000 | Lange ......................... 606/61 |

* cited by examiner

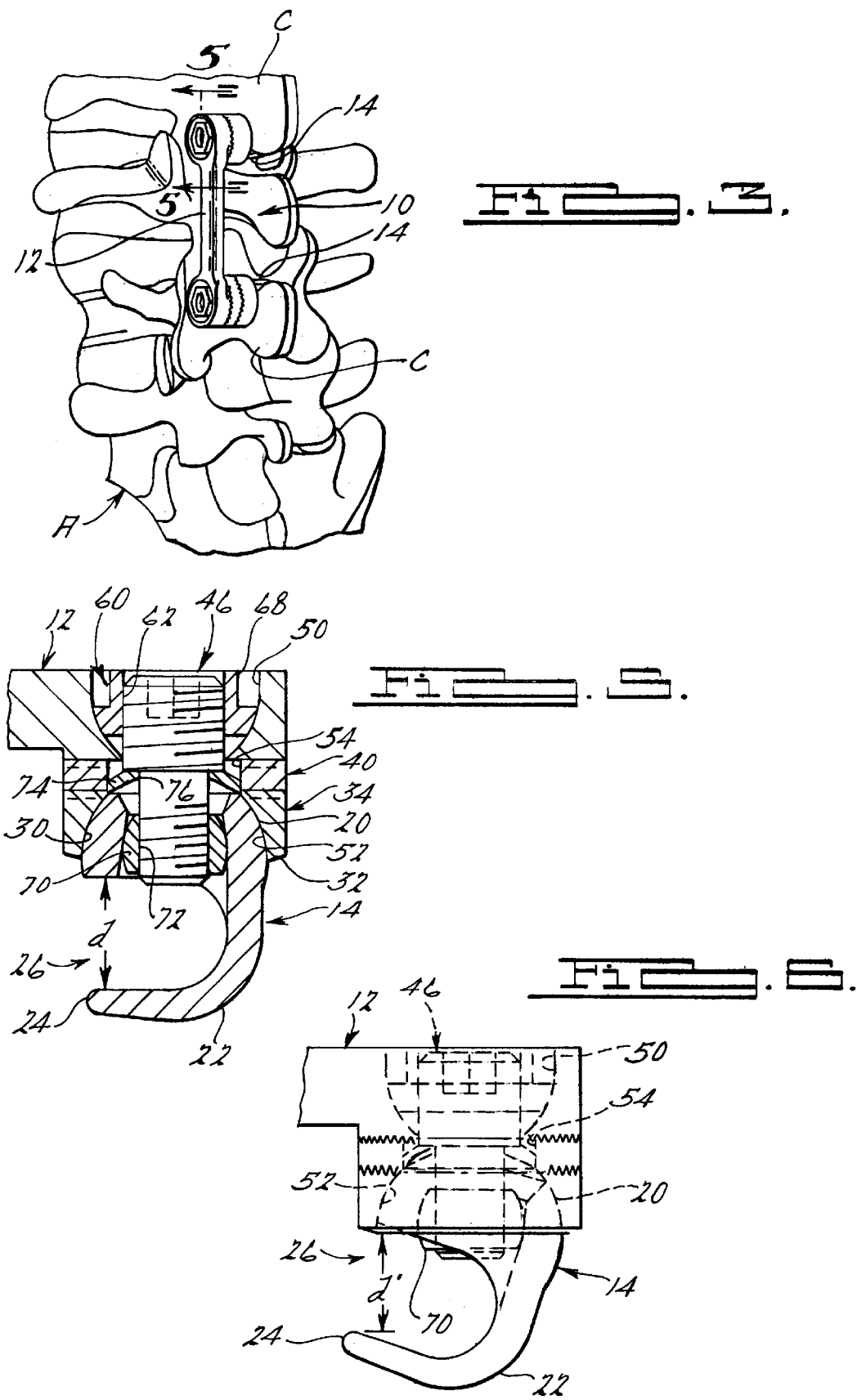

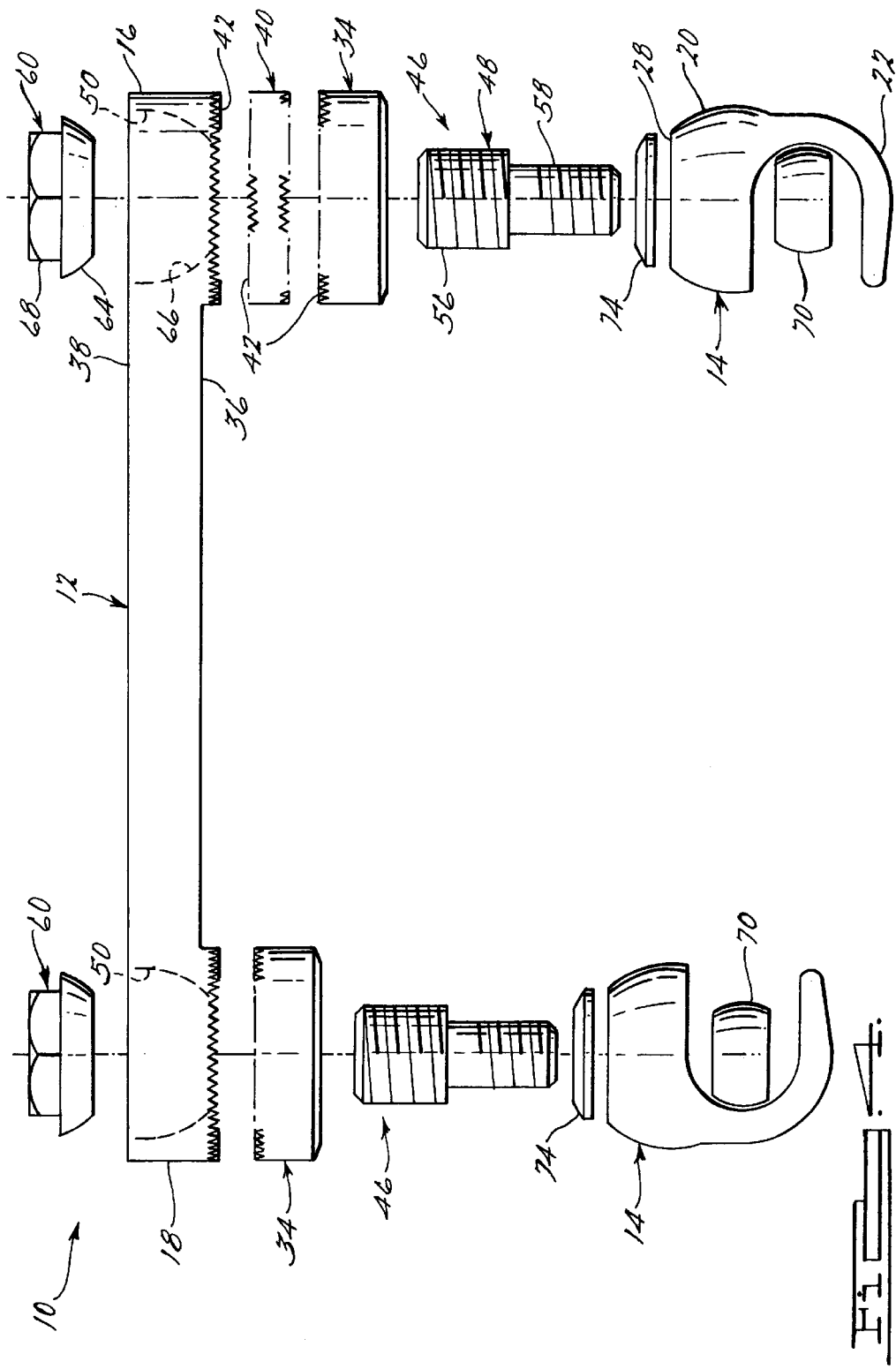

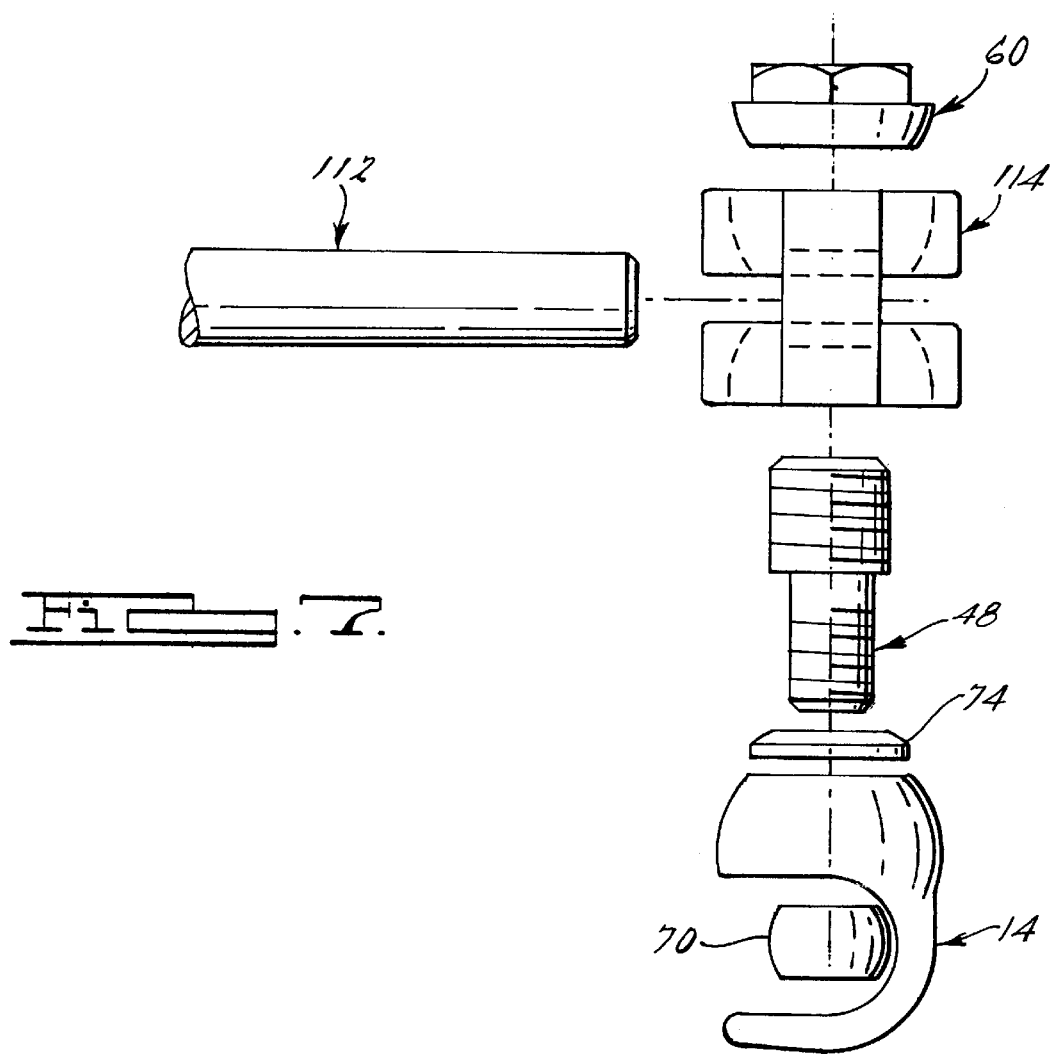
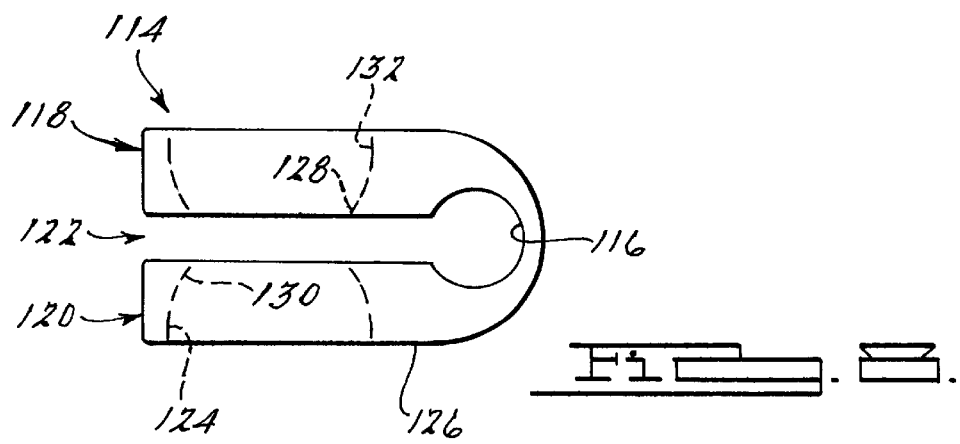

METHOD AND APPARATUS FOR SPINAL FIXATION

BACKGROUND OF THE INVENTION

1. Field of the Invention

The present invention relates generally to the field of spinal fixation devices. More specifically, the present invention is directed to a method and apparatus for spinal fixation which incorporate a polydirectional hook for engaging the spine.

2. Description of the Related Art

The human spinal column includes more than twenty discrete bones. These bones are generally similar in shape. Despite their similar shape, however, they do vary substantially in size in accordance with their individual position along the spinal column. The bones are anatomically categorized as being members of one of three classifications: cervical, thoracic, or lumbar. The cervical portion of the spinal column, which comprises the top of the spine up to the base of the skull, includes the first seven vertebrae. The intermediate twelve bones are thoracic vertebrae. The remaining five bones are the lumbar vertebrae.

With reference to FIGS. 1 and 2, a portion of the human spinal column A is shown. The spinal cord B is housed in a central canal and protected from the posterior side by a shell of bone called the lamina C. Each of the lamina C have three large protrusions. Two of the protrusions extend laterally from the side ends thereof and are referred to as the transverse processes D. The third protrusion extends back and down from the center of the lamina C and is called the spinous process E.

The anterior portion of the spine includes a set of generally cylindrically shaped bones stacked one on top of the other which are referred to as the vertebral bodies F. The vertebral bodies are separated from one another by cartilage spacers referred to as intervertebral discs G. Bone bridges referred to as pedicles H couple the anterior vertebral body F to the corresponding lamina C and posterior elements D and E.

The spinal column is a highly complex structure which houses and protects critical elements of the nervous system. In spite of these complexities, the spinal column is a highly flexible structure, capable of a high degree of curvature and twist through a wide range motion. Genetic or developmental irregularities, trauma, chronic stress, tumors, and disease, however, can result in spinal pathologies which either limit this range of motion, or threaten the critical elements of the nervous system housed within the spinal column.

A variety of systems have been disclosed in the art which achieve immobilization of portions of the spinal column by implanting artificial assemblies in or on the spinal column. These assemblies may be generally classified as anterior, posterior or lateral implants. Posterior implants are attached to the back of the spinal column generally by coupling to the pedicles with screws, or through hooks which attach under the lamina. In either case, the implants generally include elongate support rod elements which are coupled to the screws or hooks to immobilize several sequential vertebrae, for example to hold them stable so that adjacent bones may be fused with bone graft.

Such hook and rod assemblies generally comprise a plurality of hooks having rounded blade portions which are inserted posteriorly under the lamina between the transverse process and the spinous process. Difficulty may be encountered with the insertion of hooks under sequential lamina. In this regard, fixed hooks of the prior art are not able to self align in the sagittal and coronal planes. Correction of this difficulty requires time consuming reshaping of the rods or links used to connect the hooks. Such bending is a tedious process, which is inconsistent and adds unwanted time to an operation. In the event that the hooks are not securely fastened to the lamina, relative motion at the bone interface may lead to pseudoarthrosis or other ailments.

It is often the case that the failure of a hook is related to improper throat diameter. It is desirable to have lamina hooks offer the ability to adjust the throat diameter by changing the angle of the hook body to the rod or link. An adjustable throat diameter facilitates fixation on various locations of the spine and different size patients.

To a limited extent, it is also known to employ spinal fixation systems having a hook device adjustably carried by a rod. For example, U.S. Pat. No. 5,578,033 discloses a rod receiving body mounted to a blade portion such that the body may be maneuvered relative to the placement of the blade. The blade portion of the disclosed device has a semi-spherical head portion which sits above the lamina. The rod receiving portion is a separate coupling arrangement having lower, intermediate, and upper portions. The lower portion is slotted and tapered, and has a semi-spherical interior chamber in which the semi-spherical head is disposed. The intermediate portion has a side recess for receiving the rod. The top portion is threaded for a top locking nut. A locking ring is disposed about the coupling arrangement. A rod retaining sleeve is provided about the coupling arrangement. The sleeve has a lower surface which seats against the top of the rod.

While the device disclosed by U.S. Pat No. 5,578,033 may be suitable for certain applications, it is associated with certain disadvantages. For example, the clamping force for arresting movement of the hook relative to the rod is indirectly applied in an inefficient manner. In this regard, when the rod is in place, the locking nut is tightened to provide a downward force onto the sleeve. The sleeve, in turn, applies a force against the rod, which causes the locking ring to descend down the tapered lower portion, therein locking the semi-spherical head in the interior chamber of the coupling arrangement, and locking it into position relative to the blade portion. In addition, the adjustable hook disclosed by U.S. Pat. No. 5,578,033 is not adapted to be used with a plate or link system. The present invention is specifically intended to overcome these specific disadvantages, among others, associated with devices heretofore proposed.

SUMMARY OF THE INVENTION

According to one aspect, the present invention relates to an improved apparatus for spinal fixation which includes a hook member and a connector member such as a plate, link or rod which can be used for spinal stabilization.

An advantage of the present invention is to provide a method and apparatus for spinal fixation that incorporate a connector member and an improved polydirectional spinal hook.

Another advantage of the present invention is to provide a method and apparatus for spinal fixation that allows for hook alignment in both the sagittal and coronal planes without the need to bend the longitudinal member.

Another advantage of the present invention is to provide a method and apparatus for spinal fixation which offers the ability to adjust the throat diameter of a hook by changing the angle of the hook body, to thereby facilitate fixation on various locations of the spine and different size patients.

It is another advantage of the present invention to provide a polydirectional hook assembly for spinal fixation which more efficiently applies a clamping force for arresting relative rotation between a connector member and the hook assembly.

BRIEF DESCRIPTION OF THE DRAWINGS

FIG. 3 is a perspective view of an apparatus constructed in accordance with the teachings of a first preferred embodiment of the present invention illustrated operatively attached to lamina of the human spinal column.

FIG. 4 is an enlarged and partially exploded side view of the apparatus of FIG. 2 according to the teachings of the preferred embodiment of the present invention.

FIG. 5 is a cross-sectional view taken along the line 5—5 of FIG. 3, illustrating the hook member oriented in a first position relative to the linkage member.

FIG. 6 is an enlarged side view of a portion of the apparatus of the second preferred embodiment of the present invention illustrated with the hook member rotated to a second position relative to the linkage member.

FIG. 7 is a partially exploded side view of a portion of an apparatus constructed in accordance with the teachings of a second preferred embodiment of the present invention.

FIG. 8 is an end view of the rod clamp of FIG. 7.

DETAILED DESCRIPTION OF THE PREFERRED EMBODIMENT

Figure 1:
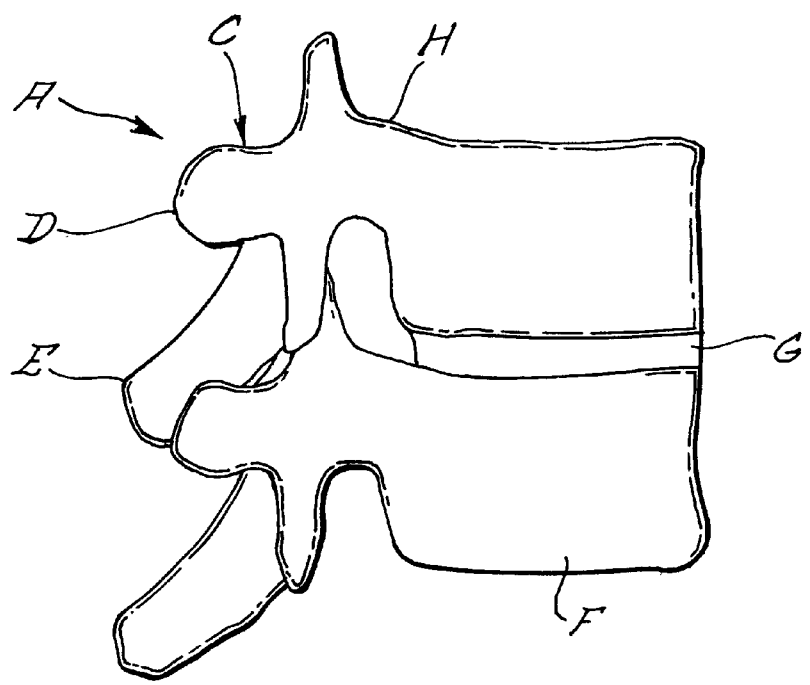
FIG. 1 is a side view of a vertebral bone characteristic of those of the cervical, thoracic and lumbar portions of the human spinal column.
Figure 2:
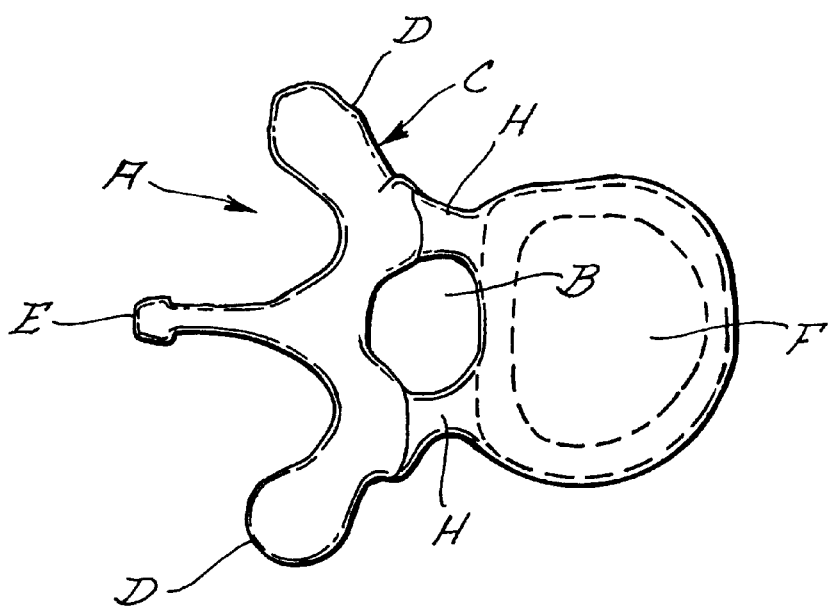
FIG. 2 is a top view of sequentially aligned vertebral bones, such as are found in the cervical, thoracic or lumbar portions of the human spinal column.

The following description of the preferred embodiment of the present invention is merely exemplary in nature and is in no way intended to limit the subject invention or its application or uses.

With initial reference to FIG. 3, an apparatus constructed in accordance with the teachings of the first preferred embodiment of the present invention is generally identified with reference 10. The apparatus 10 is illustrated operatively attached to a portion of a spinal column A of a human patient. The apparatus 10 is shown to generally include a linkage 12 and a plurality of hook members 14 for engaging lamina C of the spinal column A. As used throughout this detailed description, the term linkage will be understood to encompass plates, rods or other structure for interconnecting a pair of hook members 14. In the exemplary embodiment, the linkage 12 is shown to include a generally flat plate 38.

In the particular construction illustrated, the apparatus 10 is shown to include a pair of hook members 14. However, it will become apparent to those skilled in the art that any particular number of hook members 14 may be employed through modification of the linkage 12. In the apparatus 10 of the present invention, at least one of the hook members 14 is polyaxially mounted to the linkage 12. In the exemplary embodiment illustrated, both of the hook members 14 are polyaxially mounted to the linkage 12.

With continued reference to FIG. 3 and additional reference to FIGS. 4 through 6, the apparatus 10 of the present invention will be described in further detail. A significant portion of the remainder of this detailed description will focus upon a first end 16 of the linkage 12, associated one of the hook members 14, and associated means for polyaxially mounting the hook member 14 to the linkage 12. A second end 18 of the linkage 12 and its associated hook member 14 will be understood to be substantially identical. Differences there between will be addressed below.

The hook member 14 of the present invention is illustrated to generally include an upper portion 20 and a lower portion 22. The lower portion 22 has a curved shape for engaging the lamina C. More particularly, the lower portion 22 includes a flat blade 24 which is understood to be the portion which is inserted under the lamina C of the patient's spine A. The upper portion 20 and lower portion 22 cooperate to define an opening or throat 26 for receiving the lamina C.

The upper portion 20 of the hook member 14 includes an articular surface which is generally arcuate. In the first preferred embodiment, the articular surface is semi-spherical. As illustrated, the semi-spherically shaped upper portion 20 is truncated to include a generally flat upper surface 28.

The linkage 12 defines a cooperating articular surface 30 in an undersurface 32 thereof for matingly receiving the upper portion 20 of the hook member 14. The articular surface 30 defined by the linkage 12 is also semi-spherical. The interface between the articular surfaces 20 and 30 thereby provides polyaxial or universal movement of the hook member 14 relative to the linkage 12.

In the embodiment illustrated, the linkage 12 includes a cap member 34 which defines the articular surface 30. The cap member 34 may be placed immediately adjacent an underside 36 of the generally flat plate 38 of the linkage 12 as shown at the second end 18 in the exploded view of FIG. 4. Alternatively, a spacer 40 may be interdisposed between the cap member 34 and the flat plate 38. In either case, the interfacing surfaces between these elements are shown to include radially arranged serrations 42 for providing adjustability therebetween. The spacer 40 accommodates depth differences between adjacent lamina C. It will be understood that two or more spacers 40 may alternatively be used together.

The apparatus 10 of the present invention is further shown to include a coupling arrangement 46 for adjustably interconnecting each of the hook members 14 with a respective end of the linkage 12. The coupling arrangement 46 includes a shaft 48 which passes through an aperture 50 provided in the end 16 of the linkage 12 and an aligning aperture 52 provided in the cap member 34 of the linkage 12. Where a spacer 40 is provided, the shaft 48 similarly passes through an aligning aperture 54 provided therein. The shaft 48 includes an upper portion 56 having a first diameter and a lower portion 58 having a second diameter. In the embodiment illustrated, the diameter of the upper portion 56 is greater than the diameter of the lower portion 58 and both the upper and lower portions 56 and 58 are externally threaded.

The coupling arrangement 46 further includes a locking nut 60 having an internally threaded aperture 62 for meshingly receiving the external threads of the upper portion 56 of the shaft 48. The locking nut 60 includes a partially spherical lower portion 64 adapted to seat within a complimentary recess 66 provided in the end 16 of the linkage 12. The locking nut 60 is further shown to include an upper portion 68 which is hexagonal in shape for receiving a conventional tightening tool (not shown). The locking nut 60 functions to align the shaft 48 perpendicular to the linkage 12.

The coupling arrangement 46 is further shown to include a locking member 70 carried by the lower end 58 of the shaft 48. The locking member 70 defines an aperture 72 which is internally threaded for meshingly receiving the external threads of the lower portion 58 of the shaft 48. In the first preferred embodiment, the locking member 70 is welded to the lower portion 58 of the shaft 48 to prevent relative movement therebetween. The locking member 70 is disposed within a lower portion of the aperture 52 which upwardly tapers.

The coupling element 46 of the present invention is further shown to include a washer 74 having an aperture 76 through which the shaft 48 passes. The washer 74 is shown disposed within the aperture 54 of the spacer 40 and has an outer diameter larger than an upper end of the aperture 52 provided in the upper portion 20 of the hook member 14. The washer 74 operates to retain the shaft 48 within the aperture 52 of the hook member 14 when the hook member 14 is not engaged with the linkage 12. In addition, the washer 74 operates to prevent excessive downward translation of the shaft 48.

In operation, the surgeon engages a portion of the spine with the lower portion 22 of the hook member 14 while the locking nut 60 is loosely retained on the upper threaded portion 56 of the shaft 48. The hook member 14 is permitted to polyaxially move relative to the linkage 12 thereby allowing for alignment in both the sagittal and coronal planes without the need to bend or otherwise reconfigure the linkage 12. This polyaxial movement of the hook member 14 relative to the linkage 12 is shown, for example, in FIGS. 5 and 6.

In the cross-sectional view of FIG. 5, the lower blade 24 is oriented in a first position generally parallel to the linkage 12 and a first throat diameter d is defined for receiving the lamina C. In FIG. 6, the hook member 14 has been rotated clockwise to a second position, effectively reducing the throat diameter d' through adjustment of a hook member angle. Once the desired angle of the hook member 14 relative to the linkage 12 is established, the locking nut 60 is tightened. Tightening of the locking nut 60 serves to draw the shaft 48 upward, in turn directly establishes a clamping force between the articular surfaces 20 and 30 of the hook member 14 and the linkage 12, respectively. As a result, relative movement therebetween is prevented.

Turning to FIGS. 7 and 8, an apparatus constructed in accordance with the teachings of the second preferred embodiment of the present invention is generally identified with reference 110. The apparatus 110 of the second preferred embodiment will be understood to include various elements substantially identical to elements of the apparatus 10 of the first preferred embodiment. In this regard, the apparatus 110 of the second preferred embodiment is illustrated to include the hook member 14, shaft 48, locking nut 60, locking member 70, and washer 74 of the apparatus 10 of the first preferred embodiment. Reference numeral introduced in connection with the apparatus 10 of the first preferred embodiment are used to identified common features of the apparatus 100 of the second preferred embodiment.

With particular reference to FIG. 7, the apparatus 110 of the second preferred embodiment is shown to differ from the apparatus 10 of the second preferred embodiment primarily in that it incorporates a cylindrical rod 112 rather than the generally flat plat 38. As with the first preferred embodiment, it will be understood that the apparatus 110 of the second preferred embodiment includes a second end (not shown) substantially identical to the first end shown in the exploded view of FIG. 7.

The apparatus 110 is illustrated to include a rod clamping member 114. The rod clamping member 114 and the cylindrical rod 112 cooperate to effectively form a linkage for interconnecting a pair of hook members 14. As illustrated, the rod clamping member 114 is generally C-shaped defining an aperture 116 for receiving the rod 112. The rod clamping 114 further includes upper and lower flanges 118 and 120, respectively, which are spaced apart by a gap 122.

The lower flange 120 of the rod clamping member 118 defines an articular surface 124 in an undersurface 126 thereof for matingly receiving the upper portion 20 of the hook member 14. The articular surface 124 is preferably semi-spherical. The interface between the articular surfaces 20 and 124 provides polyaxial or universal movement of the hook member 14 relative to the rod clamping member 114.

In the apparatus 110 of second preferred embodiment, shaft 48 passes through an aperture 128 provided in the upper flange 118 of the rod clamping member 114. The shaft 48 also passes through an aligning aperture 130 provided in the lower flange 120. The locking nut 60 seats within a complimentary recess 132 provided in the upper flange 118.

As with the first preferred embodiment, the surgeon engages a portion of the spine (for example, the lamina) with the lower portion 22 of the hook member 14 while the locking nut 60 is loosely retained on the upper threaded portion 56 of the shaft 48. The hook member 14 is permitted to polyaxially move relative to the linkage 12 thereby allowing for alignment in both the sagittal and coronal planes without the need to bend or otherwise reconfigure the linkage 12. In addition, the rod clamping members 114 may be translated longitudinally along the axis of the cylindrical rod 112.

Once the desired angle of the hook member 14 relative to the rod 112 and the longitudinal spacing between the hook members 14 are established, the locking nut 60 is tightened. Tightening of the locking nut 60 serves to draw the shaft 48 upward, in turn directly establishing a clamping force between the articular surfaces 20 and 30 of the hook member 14 and the linkage 12, respectively. As a result, relative movement therebetween is prevented. Such tightening of the locking nut 60 also serves to reduce the effective diameter of the aperture 116, thereby clamping the rod clamping member 114 to the rod 112.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. An apparatus for fixation of a spine, the apparatus comprising:
   a linkage having a longitudinal axis;
   a hook member including an upper portion and a lower portion, said lower portion having a curved shape for engaging a portion of the spine, the upper portion defining an aperture; and a coupling arrangement interconnecting said linkage and said hook member, said coupling arrangement including a shaft threadably interconnecting said linkage and said hook member and oriented substantially perpendicular to said longitudinal axis of said linkage, said coupling arrangement operative to selectively permit universal movement of said hook member relative to said linkage, said coupling arrangement including a locking member disposed in said aperture and carried by said shaft.

2. The apparatus for fixation of a spine of claim 1, wherein said upper portion matingly engages an adjacent surface of said linkage.

3. The apparatus for fixation of a spine of claim 1, wherein said upper portion is partially spherical and defines the aperture.

4. The apparatus for fixation of a spine of claim 1, wherein said shaft rotatable in a first direction to draw said upper portion toward said linkage.

5. The apparatus for fixation of a spine of claim 1, wherein said locking member has the shape of a truncated hollow cone.

6. The apparatus for fixation of a spine of claim 1, wherein said lower portion of said hook member defines a throat diameter having a length generally perpendicular to said linkage, said length of said throat diameter being adjustable in response to movement of said hook member relative to said linkage, said linkage defining a recess matingly receiving said upper portion, said recess adapted to receive a portion of said length as said hook member is rotated relative to said linkage.

7. An apparatus for fixation of a spine, the apparatus comprising:

a hook member including an upper portion and a lower portion, said lower portion having a curved shape for engaging a portion of the spine;

a linkage including a generally cylindrical rod and a rod clamping member, said linkage defining a longitudinal axis; and a coupling arrangement interconnecting said linkage and said hook member so as to selectively permit universal movement of said hook member relative to said linkage, said coupling arrangement including a shaft threadably interconnecting said linkage and said hook member and oriented substantially perpendicular to said longitudinal axis of said linkage;

wherein said rod clamping member includes an upper flange and a lower flange, said lower flange comprising said adjacent surface of said linkage, said upper flange defining a partially cylindrical recess receiving a locking nut threadably receiving an upper portion of said shaft.

8. The apparatus for fixation of a spine of claim 7, wherein said upper portion matingly engages an adjacent surface of said linkage.

9. The apparatus for fixation of a spine of claim 8, wherein said upper portion is partially spherical and defines an aperture for receiving said shaft.

10. The apparatus for fixation of a spine of claim 9, wherein said shaft is rotatable in a first direction to draw said upper portion toward said linkage.

11. The apparatus for fixation of a spine of claim 7, wherein the upper portion defines an aperture and said coupling arrangement further includes a locking member disposed in said aperture and carried by said shaft, said locking member having the shape of a truncated hollow cone.

12. The apparatus for fixation of a spine of claim 7, wherein said lower portion of said hook member defines a throat diameter having a length generally perpendicular to said linkage, said length of said throat diameter being adjustable in response to movement of said hook member relative to said linkage, said linkage defining a recess matingly receiving said upper portion, said recess adapted to receive a portion of said length as said hook member is rotated relative to said linkage.

13. An apparatus for fixation of a spine, the apparatus comprising:

a linkage having a longitudinal axis;

a hook member including an upper portion and a lower portion, said lower portion having a curved shape for engaging a portion of the spine; and a coupling arrangement interconnecting said linkage and said hook member, said coupling arrangement including a shaft threadably interconnecting said linkage and said hook member and oriented substantially perpendicular to the longitudinal axis at the linkage, said coupling arrangement operative to selectively permit universal movement of said hook member relative to said linkage;

wherein said linkage further includes a generally flat plate and a cap removably attached to said generally flat plate, said cap defining a partially spherical recess matingly engaging said upper portion and including an aperture for receiving said shaft.

14. An apparatus for fixation of a portion of a spine, the apparatus comprising:

a hook member including a partially spherical upper portion and a lower portion having a curved shape for engaging a portion of the spine;

a linkage defining a longitudinal axis; and a coupling arrangement interconnecting said linkage and said hook member, said coupling arrangement including a shaft defining a shaft axis threadably interconnecting said linkage and said hook member and oriented generally substantially perpendicular to said linkage, said coupling arrangement operative to selectively permit universal movement of said hook member relative to said linkage about said shaft axis;

wherein said coupling arrangement further includes a locking nut having engaged an upper portion of said shaft, said locking nut having a spherical portion matingly received within a recess in an upper surface of said linkage.

15. The apparatus for fixation of a spine of claim 14, wherein said upper portion defines an aperture and said coupling arrangement further includes a locking member disposed in said aperture and carried by said shaft, said locking member threadably engaged by said shaft and having the shape of a truncated hollow cone.

16. The apparatus for fixation of a spine of claim 14, wherein said lower portion of said hook member defines a throat diameter having a length generally perpendicular to said linkage, said length of said throat diameter being adjustable in response, to movement of said hook member relative to said linkage, said linkage defining a recess matingly receiving said upper portion, said recess adapted to receive a portion of said length as said hook member is rotated relative to said linkage.

17. The apparatus for fixation of a spine of claim 14, wherein said linkage includes a generally flat plate.

18. The apparatus for fixation of a spine of claim 14, wherein said linkage further includes a cap removably attached to said generally flat plate, said cap defining a partially spherical recess matingly engaging said upper portion and including an aperture for receiving said shaft.

19. The apparatus for fixation of a spine of claim 14, wherein said shaft includes an upper portion threadably engaging said locking nut.

20. The apparatus for fixation of a spine of claim 14, wherein said coupling arrangement is further operative for clamping said hook member relative to said linkage member and preventing relative movement therebetween.

* * * * *